United States Patent [19]

Ward

[11] 4,281,132
[45] Jul. 28, 1981

[54] PIPERIDINO UREAS AND THIOUREAS

[75] Inventor: Terence J. Ward, Slough, England

[73] Assignee: John Wyeth & Brother Limited, Maidenhead, England

[21] Appl. No.: 954,147

[22] Filed: Oct. 24, 1978

[30] Foreign Application Priority Data

Oct. 29, 1977 [GB] United Kingdom ............... 45142/77

[51] Int. Cl.³ .......................................... C07D 211/58
[52] U.S. Cl. .................... 546/224; 546/213; 546/214; 424/267
[58] Field of Search ................. 546/224, 213, 214; 424/267

[56] References Cited

U.S. PATENT DOCUMENTS 3,992,389  11/1976  Cavalla et al. ..................... 546/224
4,073,790  2/1978  Archibald et al. .................. 546/224

Primary Examiner—Norma S. Milestone
Attorney, Agent, or Firm—Arthur E. Wilfond

[57] ABSTRACT

Compounds of formula

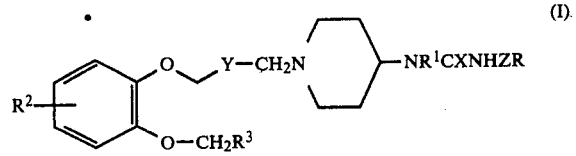

in which
X represents oxygen or sulphur;
Y represents —CHOH— or

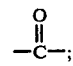

Z represent

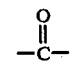

or a direct bond;
R represents cycloalkyl group having 5 to 7 carbon atoms or an optionally substituted aryl or heteroaryl radical, or when —Z— is a direct bond R also represents hydrogen;
R¹ represents hydrogen or lower alkyl;
R² represents hydrogen, halogen, lower alkyl or lower alkoxy; and
R³ represents hydrogen or lower alkyl, and a pharmaceutically acceptable acid addition or quarternary ammonium salts thereof, are disclosed which possess hypotensive activity.

1 Claim, No Drawings

PIPERIDINO UREAS AND THIOUREAS

This invention relates to piperidine derivatives having pharmaceutical activity, to processes for their preparation, to pharmaceutical compositions containing them and to intermediates useful in their preparation.

More particularly this invention provides compounds having the formula:

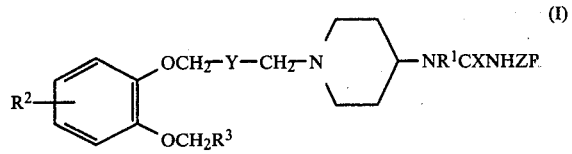

or a pharmaceutically acceptable acid addition or quaternary ammonium salt thereof, wherein X represents oxygen or sulphur, Z represents —CO— or a single bond, R represents cycloalkyl having 5 to 7 ring carbon atoms, or an optionally substituted aryl or heteroaryl radical, or when Z is a single bond R also represents hydrogen; $R^1$ is hydrogen or lower alkyl; $R^2$ is hydrogen, halogen, lower alkyl or lower alkoxy; $R^3$ is hydrogen or lower alkyl, and Y is —CHOH— or —CO—.

Examples of $R^2$ are hydrogen, methyl, ethyl, propyl, chlorine, bromine, methoxy, ethoxy and propoxy.

Examples of R when other than hydrogen are: aryl radicals such as phenyl and phenyl substituted by one or more groups such as lower alkyl (e.g. methyl, ethyl, propyl or isopropyl), lower alkoxy (e.g. methoxy, ethoxy, propoxy or isopropoxy), halogen (e.g. fluorine, chlorine or bromine) perhalolower alkyl, such as trifluoromethyl, nitro, amino and hydroxy; cycloalkyl radicals such as cyclohexyl; heteroaryl radicals, wherein the heteroatom is selected from oxygen, nitrogen or sulphur, such as thienyl (e.g. 2-thienyl), furyl (e.g. 2-furyl) and pyridyl (e.g. 3-pyridyl).

Examples of $R^1$ are hydrogen methyl, ethyl, n-propyl.
Examples of $R^3$ are hydrogen and methyl.

Examples of acid addition salts are those formed with pharmaceutically acceptable acids such as hydrochloride, sulphate, phosphate, acetate, maleate, fumarate, tartrate, formate, methanesulphonate, p-toluenesulphonate, benzoate, succinate, lactate and salicylate.

Examples of quaternary ammonium compounds are those formed with alkyl and aralkyl halides, particularly methyl and ethyl halides such as ethyl bromide and methyl iodide, and benzyl halides such as benzyl chloride.

It will be apparent to those skilled in the art that the compounds of formula I may possess one asymmetric centre and hence optical isomers are possible. All such optically active forms and mixtures thereof are intended to be included within the scope of this invention. More particularly when Y represents the group —CHOH— in formula I above then one asymmetric centre is present and therefore such a compound can exist in one of two enantiomeric forms. Separation of enantiomers may be effected by standard techniques known in the art.

The compounds of this invention possess pharmaceutical activity or are intermediates for other compounds of this invention.

More particularly when Y is —CHOH— the compounds of formula I possess hypotensive activity.

In a standard test on normotensive anaesthetised rats the representative compound of formula I, 1-benzoyl-3-[1-(2-hydroxy-3-[2-methoxyphenoxy]propyl)piperid-4-yl]urea, hydrochloride monohydrate, was found to produce a marked decrease in diastolic blood pressure of >30 mm Hg sustained for 15 minutes in 3 rats at doses of 0.8, 1.6 and 3.2 mg/kg of rat body weight.

The compounds of formula I may also possess the ability to reduce heart rate when administered in a standard test on hypertensive rats. The compound of formula I mentioned above showed a marked ability to reduce heart rate in such a test producing a 43.5% and 29.5% decrease in heart rate at a time period of 2 hours and 6 hours respectively after dosing.

The test procedure used is described below:

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressure stabilises at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solutions of the test compound in 0.5% hydroxypropylmethylcellulose 0.9% saline vehicle. Blood pressures are recorded again at 2, 6 and 24 hours and the results, expressed as a percentage of the pre-dose values compared with those of a similar group of rats receiving vehicle alone.

In the aforementioned test the representative compound of formula I was also found to lower blood pressure by 17% 2 hours and 6 hours after dosing.

It is possible to interconvert the compounds of formula I and hence all the compounds are useful as intermediates for other compounds of formula I. Thus compounds of formula I wherein Y represents —CO— are useful as intermediates for preparing compounds of formula I wherein Y represents —CHOH— as shown hereinafter. Likewise the compounds of formula I wherein Y represents —CHOH— are useful for preparing compounds of formula I wherein Y represents —CO—. Compounds of formula I wherein Z is —CO— and hence R—Z— represents an acyl group, especially those as herein defined, are useful in the preparation of compounds of formula I wherein R is H, which compounds can be acylated to give other compounds of this invention. This invention also provides processes for preparing the compounds of formula I.

One such process for preparing a compound of formula I wherein X represents oxygen, and R is other than hydrogen comprises reacting a compound of formula

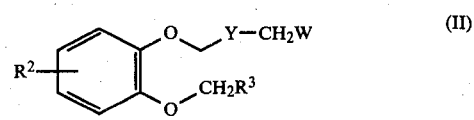

wherein $R^2$, $R^3$ and Y are as defined above in connection with formula I and W represents a halogen (e.g. chlorine or bromine) or an equivalent replaceable radical such as an organic sulphonyl radical, e.g. tosylate (-Otosyl), with a compound of formula

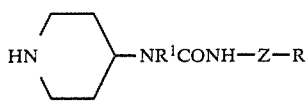

(III)

wherein X, Z, R and $R^1$ are as defined above in connection with formula I; R being other than hydrogen. Such a reaction is conveniently carried out in the presence of base, e.g. an alkali metal carbonate such as potassium carbonate or a lower alkyl amine, e.g. triethylamine, in a suitable inert solvent, e.g. dimethylformamide, dichloromethane, isopropanol and the like.

A further process for preparing compounds of formula I comprises reacting a compound of formula

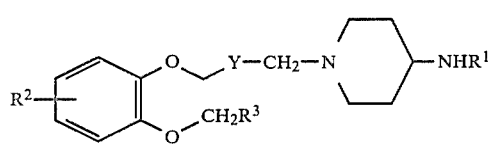

(IV)

wherein $R^1$, $R^2$, $R^3$ and Y are as hereinbefore defined with a compound of formula (V)

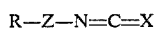 R—Z—N=C=X (V)

wherein X, R and Z are as defined in connection with formula I, R being other than hydrogen. This reaction should be conducted under mild conditions to avoid the possibility of reaction between the amine IV (when Y is —CO—) and the oxoethylene radical of another molecule of amine IV giving a Schiffs base. Usually the reaction to form the compound of formula I takes place at room temperature.

The starting materials of formula III may be prepared by reacting 1-benzyl-4-aminopiperidine with a compound of formula V wherein X is oxygen and removing the 1-benzyl group from the product by hydrogenolysis.

The starting materials of formula IV wherein $R^1$ is hydrogen may be prepared by methods described in our British Specification No. 1,345,872. The starting materials of formula (IV) wherein $R^1$ is lower alkyl may be prepared by alkylating corresponding compounds of formula IV wherein $R^1$ is hydrogen, or by methods analogous to those described in British Specification No. 1,345,872.

Compounds of formula I wherein R is hydrogen may be prepared by hydrolysis, e.g. using aqueous sodium hydroxide, of the corresponding compounds of formula

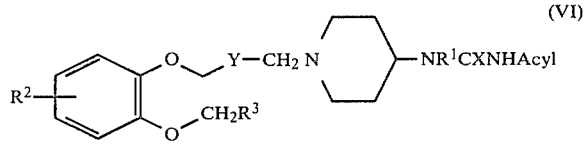

(VI)

wherein X, $R^1$, $R^2$, $R^3$ and Y are as defined above in connection with formula I and Acyl represents an acyl radical, e.g. aroyl or heteroaroyl. Once a compound of formula I wherein R is hydrogen has been prepared then that compound may be acylated to give other compounds of this invention wherein R—Z— represents an acyl radical, for example, using an active derivative of an acid of formula

 RCOOH (VII)

wherein R is cycloalkyl of 5 to 7 carbon atoms, aryl or heteroaryl. Examples of reactive derivatives of the acid of formula VII are the halide, e.g. the chloride, and the anhydride.

If necessary, in any of the reactions herein described, reactive substituent groups may be blocked during a reaction and released at a later stage.

A further method of preparing compounds of formula I wherein $R^1$ is a hydrogen and Z is a single bond comprises reacting a compound of formula

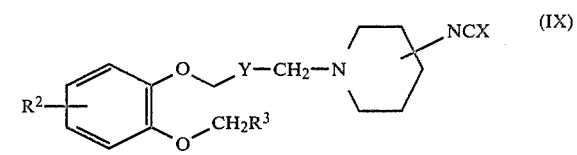

(IX)

with an amine of formula

 R NH$_2$ (X)

wherein $R^3$, $R^2$, X and Y are as defined above in connection with formula I and R is as defined in connection with formula I except hydrogen. This reaction should be conducted under mild conditions to avoid any possibility of the amine (X) reacting with the oxoethylene group to form a Schiffs base.

Compounds of formula (IX) may be prepared by treatment of a compound of formula IV, wherein $R^1$ is hydrogen with phosgene or thiophosgene followed by treatment of the product with calcium oxide according to the following reaction scheme:

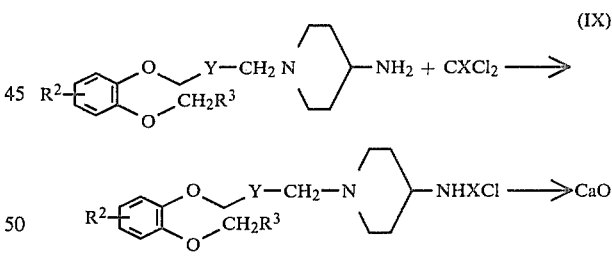

Other standard methods may be used to prepare compound (IX).

A method for preparing compounds of formula I wherein R is hydrogen comprises reacting a compound of formula IV with nitrourea ($H_2NCONH.NO_2$).

The compounds of formula (I) wherein Y is —CHOH— are also obtained by reacting a compound of formula

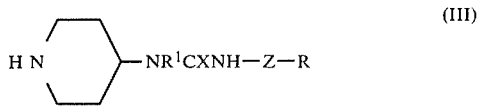

(III)

with a epoxide of formula

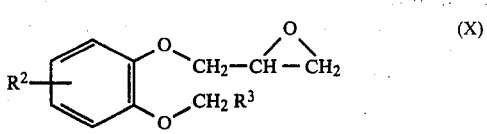

in a suitable organic solvent such as an aromatic hydrocarbon for example, benzene, toluene, xylene and the like; a halogenated hydrocarbon such as chloroform and methylene chloride; or a lower alkanol, such as, for example, methanol, ethanol, 2-propanol and the like and preferably in a mixture of an aromatic hydrocarbon and a lower alkanol. The reaction may be promoted by the addition of alkali.

Once a compound of formula I wherein Y is —CO— has been prepared then such a compound may be reduced to give other compounds of formula I wherein Y is —CHOH—. For example reduction may be effected with a hydride transfer agent such as an alkali metal borohydride, e.g. sodium borohydride, and sodium tri-t-butoxyborohydride. Other methods applicable to the reduction of a ketone to a secondary alcohol are known in the literature—see for example "Compendium of Organic Synthetic Methods" Ian T. Harrison, Shuven Harrison, published by Wiley Interscience, Volume I, 1971.

Once a compound of formula I wherein Y is —CHOH— has been prepared then such a compound may be oxidised to give other compounds of formula I wherein Y is —CO—. For example, chromic acid oxidation may be used to effect the above mentioned conversion. Other methods for oxidising secondary alcohols to ketones are known in the literature see, for example, the above mentioned textbook of Harrison and Harrison.

Resolution of enantiomers may be effected by standard techniques known in the art after any of the above mentioned processes where racemic starting materials are employed.

Alternatively it will be apparent to those skilled in the art that if it is desired to prepare a final product having a specific stereochemistry then it is possible in some instances to employ a starting material already having the desired stereochemistry.

The invention also includes pharmaceutical compositions containing as active ingredient an active compound of formula I as above defined wherein Y is —CHOH—. The active compound may be micronised if desired. In addition to the active ingredient, the compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient.

The following examples illustrate the invention:

EXAMPLE 1

1-Benzoyl-3-[1-(2-hydroxy-3-[2-methoxyphenoxy]-propyl)piperid-4-yl]urea

4-Benzoylureido piperidine (1.3 g, 0.55 m), and 2,3-epoxypropoxy)anisole (0.9 g, 0.5 m) were refluxed for 24 hours in isopropylalcohol (50 cm$^3$). The solution was allowed to cool and the crystallised solid filtered off. The solid (free base) was dissolved in the least amount of chloroform, put onto an alumina column, and the column eluted with chloroform to give the title compound. The title compound was converted to its hydrochloride by dissolving it in the least amount of methanol and acidifying with ethanolic HCl. The resulting crystallised salt was filtered off. (0.53 g, 22%).

Melting Pt. 186°–188°

Microanalysis $C_{23}H_{29}N_3O_5 \cdot HCl \cdot H_2O$ requires C, 57.32%; H, 6.69%; N, 8.72%; found C, 57.75% H, 6.66%; N, 8.51%

Note: it is expected that the use of excess 2-(2,3-epoxypropoxy)anisole would make it unnecessary to perform the column chromatography purification step.

EXAMPLE 2

1-(2-Methoxyphenoxy)-3-(4-[3-(4-methoxybenzoylureido)]piperid-1-yl)propan-2-ol 2-(2,3-Epoxypropoxy)anisole (0.99 g 0.0055 m) and 1-(4-methoxybenzoyl)-3-(piperid-4-yl) urea (1.39 g, 0.005 m) in isopropyl alcohol (50 cm$^3$) were refluxed for 24 hours. The solution was cooled and the solid filtered off. This was dissolved in ethanol and acidified with ethanolic hydrogenchloride. The solution was then evaporated and the residue treated with acetone. The precipitated solid was recrystallised from isopropyl alcohol to give the title compound as the hydrochloride salt (0.7 g) m.p. 203°–205° C.

$C_{24}H_{31}N_3O_6$·HCl requires: C, 58.35%; H, 6.53%; N, 8.51%. Found: C, 58.71%; H, 6.72%; N, 8.22%.

EXAMPLE 3

1-(4-[3-(4-Fluorobenzoyl)ureido]piperid-1-yl)-3-(2-methoxyphenoxy)propan-2-ol 2-(2,3-Epoxypropoxy)anisole (0.99 g, 0.0055 m) and 1-(4-fluorobenzoyl)-3-(piperid-4-yl)urea (1.32 g, 0.005 m) in isopropyl alcohol (50 cm$^3$) were refluxed for 24 hours. The solution was cooled and the product which crystallised was filtered off. This was dissolved in ethanol and acidified with ethanolic hydrogen chloride. The solution was heated on a water bath and ethyl acetate was added to replace the lost solvent. The product crystallised out and was recrystallised twice from ethanol giving the title compound as the hydrochloride, hemihydrate (0.44 g) m.p. 194°–195° C.

$C_{23}H_{28}FN_3O_5$·HCl ½$H_2O$ requires: C, 56.26; H, 6.16; N, 8.56. Found: C, 55.91; H, 6.26; N, 8.50.

EXAMPLE 4

1-(2-Methoxyphenoxy)-3-(4-[3-phenylureido]piperid-1-yl)propan-2-ol 4-(3-Phenylureido)piperidine (1.09 g, 0.005 m) and 2-(2,3-epoxypropoxy)anisole (0.9 g, 0.05 m) were refluxed in isopropyl alcohol (75 cm$^3$) for 24 hours. The solvent was evaporated and the residue dissolved in the least amount of hot ethanol and acidified with ethanolic hydrogen chloride. The solid was filtered and recrystallised from ethanol to give the title compound as the hydrochloride quarterhydrate. (0.6 g) m.p. 191–193.

$C_{22}H_{29}N_3O_4$·HCl ¼$H_2O$ requires: C 59.99; H, 6.98; N, 9.54. Found: C 59.87; H, 7.11; N, 9.77.

EXAMPLE 5

Using a procedure analogous to Example 1 the following compounds of formula I are prepared according to the reaction:

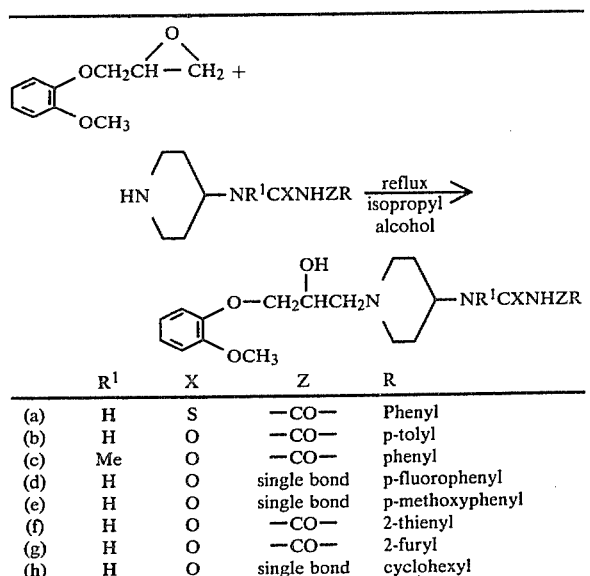

| | $R^1$ | X | Z | R |
|---|---|---|---|---|
| (a) | H | S | —CO— | Phenyl |
| (b) | H | O | —CO— | p-tolyl |
| (c) | Me | O | —CO— | phenyl |
| (d) | H | O | single bond | p-fluorophenyl |
| (e) | H | O | single bond | p-methoxyphenyl |
| (f) | H | O | —CO— | 2-thienyl |
| (g) | H | O | —CO— | 2-furyl |
| (h) | H | O | single bond | cyclohexyl |

I claim:

1. Benzoyl-3-[1-(2-hydroxy-3-[2-methoxyphenoxy]-propyl)-piperid-4-yl]urea.

* * * * *